United States Patent [19]

Ogasawara et al.

[11] Patent Number: 4,698,332
[45] Date of Patent: Oct. 6, 1987

[54] EXPECTORANT

[75] Inventors: Sadanori Ogasawara, Tokorozawa; Takashi Hanafusa, Tokyo; Katsuhide Kariya, Tokorozawa; Masayoshi Ito, Kunitachi; Yoshiyasu Shitori, Tokyo, all of Japan

[73] Assignee: Mect Corporation, Tokyo, Japan

[21] Appl. No.: 773,036

[22] Filed: Sep. 6, 1985

[30] Foreign Application Priority Data

Sep. 11, 1984 [JP] Japan .................................. 59-189950

[51] Int. Cl.$^4$ .............................................. A61K 31/70
[52] U.S. Cl. ........................................ 514/42; 424/45; 424/46
[58] Field of Search ....................... 424/45, 46; 514/42

[56] References Cited

PUBLICATIONS

Chemical Abstracts, 89:192773m (Jones), 1978.
Chemical Abstracts, 77:44614x (Behr et al), 1972.

*Primary Examiner*—Leonard Schenkman
*Attorney, Agent, or Firm*—Oblon, Fisher, Spivak, McClelland, & Maier

[57] ABSTRACT

An expectorant capable of acting on the rheological properties of sputum and capable of directly promoting the ciliary motion. The expectorant contains N-acetylneuraminic acid or a pharmaceutically active salt thereof.

8 Claims, 4 Drawing Figures

EXPECTORANT

BACKGROUND OF THE INVENTION

1. Field of the Invention

The present invention relates to an expectorant and a method of removing sputum by using the expectorant. More particularly, the invention is concerned with an expectorant made of N-acetylneuraminic acid and its pharmaceutically active salt having an effect of directly promoting ciliary motion while acting on the rheological property of sputum, as well as to a method of removing sputum by such an expectorant.

2. Description of the Related Art Including Information

Viscous secretion exists in the airway of the human body. The secretion has an important role in imparting suitable temperature and humidity to inhaled air. The matter generally referred to as "sputum" is constituted mainly by this secretion.

When its amount is moderate, the secretion in the airay, is unconsciously swallowed or expelled with the breath, but usually is never expectorated. Thus, any expectoration suggests that there is something extraordinary in the respiratory system. On the other hand, accumulation of spatum to be expectorated in the airway is liable to cause an infection via the airway. From this point of view, the removal of sputum is a matter of great significance in the medical treatment of patients who suffer with a disease in the airway.

Sputum is often very viscous and sticky so that expectoration causes the patient pain. In order to facilitate expectoration, therefore, medicine which is referred to as "expectorant" has been used. This medicine is given in a general dosage orally or by injection. The expectorant thus dosed serves to remove sputum by diluting the sputum through an increase in secretion by the mucosa of the airway, promotion of separation from the mucosa and enhancement of ciliary beat. General dosages, however, involve various clinical problems concerning mechanism and effect.

The present inventors have therefore made intensive studies and found that sialic acids can be used as a compound which is an effective expectorant which can be used in local dosages. This invention has been accomplished through a study on the sputum removing effect offered by N-acetylneuraminic acid and its salt, among the sialic acids.

SUMMARY OF THE INVENTION

Accordingly, an object of the invention is to provide an expectorant mainly composed of N-acetylneuraminic acid or its salt, as well as a method of removing sputum by local dosage of the expectorant which acts on the rheological property of spatum and which directly promotes ciliary beat such as to facilitate the expectoration.

BRIEF SUMMARY OF THE INVENTION

(A) Effective Components

Figure 1:
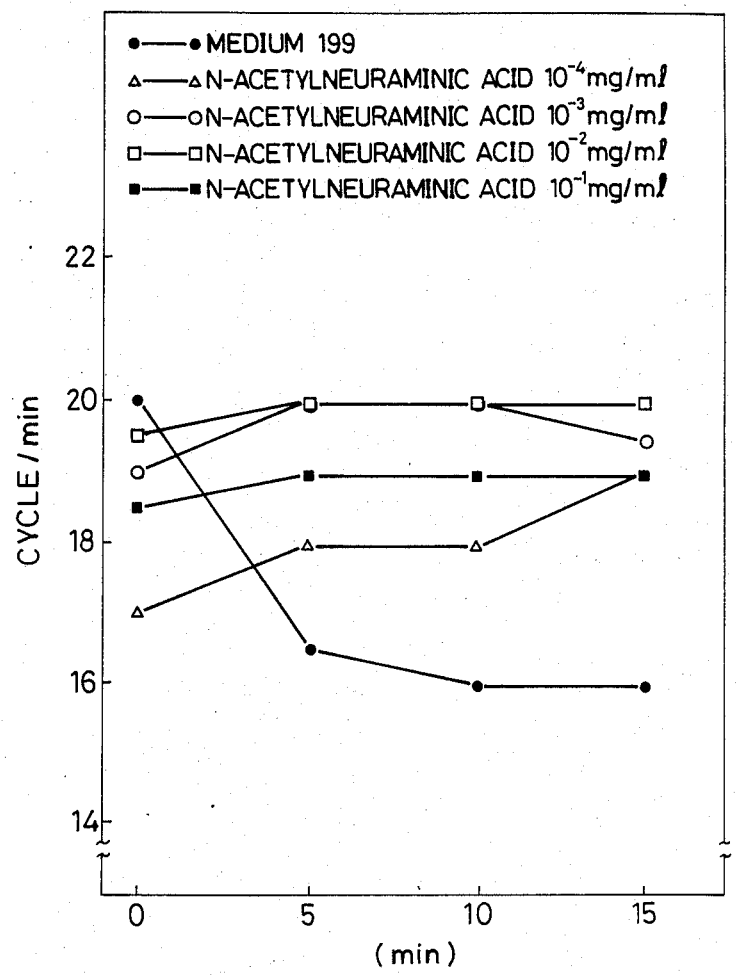
FIGS. 1 and 2 are illustrations of the effect on N-acetylneuraminic acid on the rotation of ciliated cells.

The expectorant of the invention contains, as an effective component, an N-acetylneuraminic acid or its salt which is expressed by the following general formula:

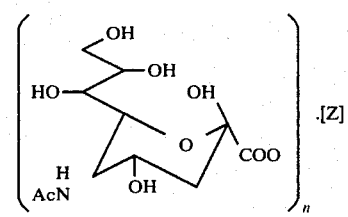

On conditiion of $n=1$, Z represents hydrogen, lithium, potassium, sodium, ammonium, organic ammonium or an organic amine, whereas, on condition of $n=2$, Z represents calcium, barium or magnesium. The N-acetylneuraminic acid itself is a known compound, and its salt can be obtained by neutralizing this acid with a hydroxide or carbonate of an alkali metal or alkali earth metal and separating the corresponding alkali metal salt or alkali earth metal salt from the system.

According to the invention, this compound is used in such a form as to permit the use of a known local dosage method such as inhalation of the pulverized compound from an aerosol.

(B) Mechanism

The effect on N-acetylneuraminic acid and its salt as an expectorant is attributable to the following two functions: namely, physiological change for easier expectoration by acting on the rheological property of expectorant such as its fluidity, yield value, spinnability, stickiness, stress relaxing time and so forth, and promotion of sputum transportation by celia through direct activation of ciliary beat of the cilia in the airway. These functions have been confirmed through an experiment in which the rotary motion of a cilium group before the application of N-acetylneuraminic acid or its salt was compared with that after the application, using celium cells in the human airway, as well as through an experiment in which the sputum conveying property of cilia of frog palatine mucosa in the state after the application of the N-acetylneuraminic acid or its salt was compared with that before the application.

(C) Form of Dosage

In clinical use, the expectorant of the invention is used in the form of, for example, the following preparation.

Example of Preparation

As the first step, N-acetylneuraminic acid or its salt is well ground and mashed in an agate mortar to reduce it to a fine powder of a grain size ranging between 1 and 20 microns. Lactose is then gradually mixed with the fine powder and diluted 10 to 20 fold. Then, 20 to 40 mg of the mixture is put in a capsule or envelope by a known method. Preferably, a capsule is used for powdered aerosol, and an envelope is used for liquid aerosol.

(D) Method of Dosage

Whether the expectorant is used as a powdered aerosol or liquid aerosol is determined on the basis of the symptoms of the patient. The does is usually 0.5 to 5 mg/time. The expectorant should be administered at least two times a day but this may be changed if the symptoms warrant it.

The results of pharmacodynamic tests and acute toxicity tests showed that the number of dosage per day need not be limited.

The expectorant is administered, when used in the form of a powdered aerosol, by means of a powder spray such as an insufflator or neubulizer, and when used as a liquid aerosol, by a liquid atomizer such as a nebulizer.

The effect of the invention can be summarized as follows; the expectorant of the invention exhibits a superior suptum removing effect when administered locally. Namely, it changes the property of sputum to ease expectoration by acting on the rheological property of sputum, e.g. yield value and viscosity. On the other hand, it directly activates the ciliated cells to promote expectoration by ciliary beat.

DESCRIPTION OF THE PREFERRED EMBODIMENTS

Description will be now made hereinunder as to the way of synthesis of the compound of the invention, as well as the effect of the same, through preferred examples.

EXAMPLE 1

Method of Synthesizing Ammonium Salt of N-Acetylneuraminic Acid 12 g of an N-acetylneuraminic acid was dissolved in 150 ml of water to form an aqueous solution into which was stirred a saturated aqueous solution of ammonium until the solution becomes neutral (pH 6.7). The reaction solution was spontaneously filtrated and the residual was freeze-dried (one day) to form 13.2 g of white crystals.

Melting Point: about 150° C. decomposed, Qualitative Reaction of Ammonium Salt: According to General Testing Method of the Pharmacopeia of Japan, 10th Edition an excess amount of sodium hydroxide reagent was added to the ammonium salt and the mixture was heated. The mixture gave off an odor of ammonium and the fume changed a red litmus paper blue.

(Elementary Analysis); N-acetylneuraminic acid ammonium 1-hydrate: $C_{11}H_{22}O_9N_2 \cdot H_2O$.

|   | Calculated value |   | Measured value |
|---|---|---|---|
| C: | 38.48% | C: | 38.11% |
| H: | 7.05% | H: | 6.92% |
| N: | 8.16% | N: | 8.17% |
| O: | 46.60% | (O: | 46.80%) |

EXAMPLE 2

Method of synthesizing N-Acetylneuraminic Acid Salts 200 ml of distilled water was added to a mixture of 10.1 g (0.0323 mole) of N-Acetylneuraminic Acid and 1.162 g (0.0162 mole) of calcium carbonate. The solution was stirred for 2 hours at room temperature until the calcium carbonate was completely dissolved (pH 6.55). The solution was filtered and the deposit was subjected to freeze-drying and decompression drying to form 11.0 g of colorless needle crystals.

Melting Point: 140° or higher (decomposed)

Qualittive Test of Calcium Salt According to General Testing Method of Pharmacopeia of Japan 10th Edition (1) A yellowish red was observed in a flame reaction test of the calcium salt.

(2) A white precipitate was observed when ammonium carbonate reagent was added to the calcium salt.

$R1V_{MAX}^{KBr}$ cm$^{-1}$): 3600–3000, 1620, 1560. (NMR(D$_2$O)ppm) 1.59–2.42 (m), 2.05(s), 3.71 (s), 3.99(s).

Salts of lithium, potassium, sodium, organic ammonium, barium and magnesium of N-acetylneuraminic acid were prepared in the same way as that described above. Namely, the N-acetylneuraminic acid was neutralized with hydroxides or carbonates of these elements, followed by freeze-drying, thus obtaining salts of N-acetylneuraminic acid.

EXAMPLE 3

Effect of N-acetylneuraminic acid and Calcium Salt of N-acetylneuramic acid on Ciliary of Palatine Mucosa of Frog (1) Test Animal Bull frogs (furnished by Saitama Test Animal) weighing 300 to 450 g were used regardless of sex.

(2) Test Material

N-acetylneuraminic acid and calcium salt of N-acetylneuraminic acid (provided by Kanto Ishiseiyaku Kabushiki Kaisha), as well as acetylcholine chloride (furnished by Sigma Kabushiki Kaisha) were used as the test substances.

(3) Test Method

Mucociliary transport was measured by the particle transport method. After decapitation of a frog, the surface of the palatine mucosa was separated with minimized damage and of fixed to a cork plate in a Petri dish which was then filled with 20 ml of Ringer's solution (trishydrochloric acid). The palatine mucosa was left in this state for 30 minutes before the commencement of measurement. For measurement, the Ringer's solution was removed and fine pieces of cork (capable of passing pharmaceutical sieve No. 5 but not capable of passing No. 6) were placed on the surface of the palatine mucosa, and the time (in seconds) required for the cork piece to move 1 cm was measured. The duration of movement, i.e., moving speed, was measured also in the state immediately after the removal of the Ringer's solution or pharmaceutical solution.

(4) Result

It was confirmed that N-acetylneuraminic acid and its calcium salt causes an acceleration of the ciliary movement of palatine mucosa in a certain dose-dependency, as will be seen from Tables 1 and 3.

This result was substantially equal to that produced by acetylcholine (control) at concentrations of $10^{-5}$ and $10^{-4}$ g/mol, as will be seen from Table 2.

(5) Judgement

N-acetylneuraminic acid and its calcium salt were confirmed as producing substantially the same ciliary movement promoting effect as the acetylcholine which has been known as being effective in the promotion of ciliary movement. N-acetylneuraminic acid and its calcium salt, therefore, are expected to facilitate expectoration. The acetylcholine, however, cannot be used as an expectorant because it causes undesirable effects such as bronchoconstriction and crinogenic action, although it promotes ciliary action. In contrast, N-acetylneuraminic acid and its calcium salt can be used as an expectorant because it effectively promotes ciliary action, without being accompanied by the detrimental effects produced by acetylcholine.

TABLE 1
Effect of N—acetylneuraminic Acid on Ciliary Movement

| Drug g/ml | | Movement (sec/cm) Frog Number | | | | Acceleration (%)* Frog Number | | | |
|---|---|---|---|---|---|---|---|---|---|
| | | 1 | 2 | 3 | 4 | 1 | 2 | 3 | 4 |
| Control | — | 32.0 | 32.7 | 40.3 | 36.0 | 0 | 0 | 0 | 0 |
| N—acetyl-neuraminic acid | $10^{-5}$ | 21.3 | 27.3 | 28.7 | 24.7 | 33.4 | 16.5 | 28.2 | 31.4 |
| | $10^{-4}$ | 17.3 | 22.0 | 20.7 | 22.0 | 45.9 | 32.7 | 48.2 | 38.9 |

$$\text{Acceleration (\%)} = \left(1 - \frac{\text{time in drug}}{\text{time in control}}\right) \times 100$$

TABLE 2
Effect of Acetylcholine on Ciliary Movement

| Drug g/ml | | Movement (sec/cm) Frog Number | | | Acceleration (%)* Frog Number | | |
|---|---|---|---|---|---|---|---|
| | | 1 | 2 | 3 | 1 | 2 | 3 |
| control | — | 45.0 | 37.0 | 39.3 | 0 | 0 | 0 |
| acetylcholine | $10^{-5}$ | 27.0 | 29.7 | 26.3 | 40.0 | 19.7 | 33.1 |
| | $10^{-4}$ | 21.0 | 21.7 | 20.7 | 53.3 | 41.4 | 47.3 |

$$\text{Acceleration (\%)} = \left(1 - \frac{\text{time in drug}}{\text{time in control}}\right) \times 100$$

TABLE 3
Effect of Calcium Salt of N—Acetylneuraminic Acid on Ciliary Movement

| Drug g/ml | | Movement (sec/cm) Frog Number | | | Acceleration (%)* Frog Number | | |
|---|---|---|---|---|---|---|---|
| | | 1 | 2 | 3 | 1 | 2 | 3 |
| control | — | 37.7 | 40.0 | 37.0 | 0 | 0 | 0 |
| calcium salt of N—acetylneuraminic acid | $10^{-5}$ | 25.0 | 29.3 | 24.3 | 33.7 | 28.0 | 34.2 |
| | $10^{-4}$ | 23.0 | 29.0 | 19.7 | 39.0 | 28.7 | 46.8 |

$$\text{Acceleration (\%)} = \left(1 - \frac{\text{time in drug}}{\text{time in control}}\right) \times 100$$

EXAMPLE 4

Effect on N-acetylneuraminic Acid and Its Calcium Salt on Rotation of Ciliated Cell (Object)

Using ciliated cells from human airway and frog palate, rotation of cell groups due to ciliary beat was observed before and after application of N-acetylneuraminic acid and calcium salt of N-acetylneuraminic acid, in order to confirm the effect of these agents on the cilitated cells.

(Method)

Human ciliated cells were collected from a normal trachea by means of a branchoscope, the ciliated cells being separated by rubbing the bronchus while observing through the branchoscope, while the collection of frog cilitated cells was conducted by rubbing the palatine mucosta, without being specially careful. The cilium cells thus obtained were floated in Medium 199 (prepared by Gibco Company) and groups of ciliated cells, each consisting of several cells exhibiting rotary motion due to ciliary motion, were sucked up by microsyringe in such a manner as to avoid damage to such cells, using observation through a phase contrast microscope. The groups of cells were transferred to a cover slip and one drop of chicken plasma (prepared by Difco Company) and one drop of 50% chicken embryo extract were added to the cells, thus forming clots. The rotary motion in the clots was recorded by means of a video recorder and the number of rotations per minute was measured. The agents were dissolved in the Medium 199 and were injected through a tube attached to a rose chamber. The state of rotary motion 5 minutes, 10 minutes and 15 minutes after the injection were recorded by means of a video recorder, and the number of revolutions was measured.

(Result)

Figure 2:
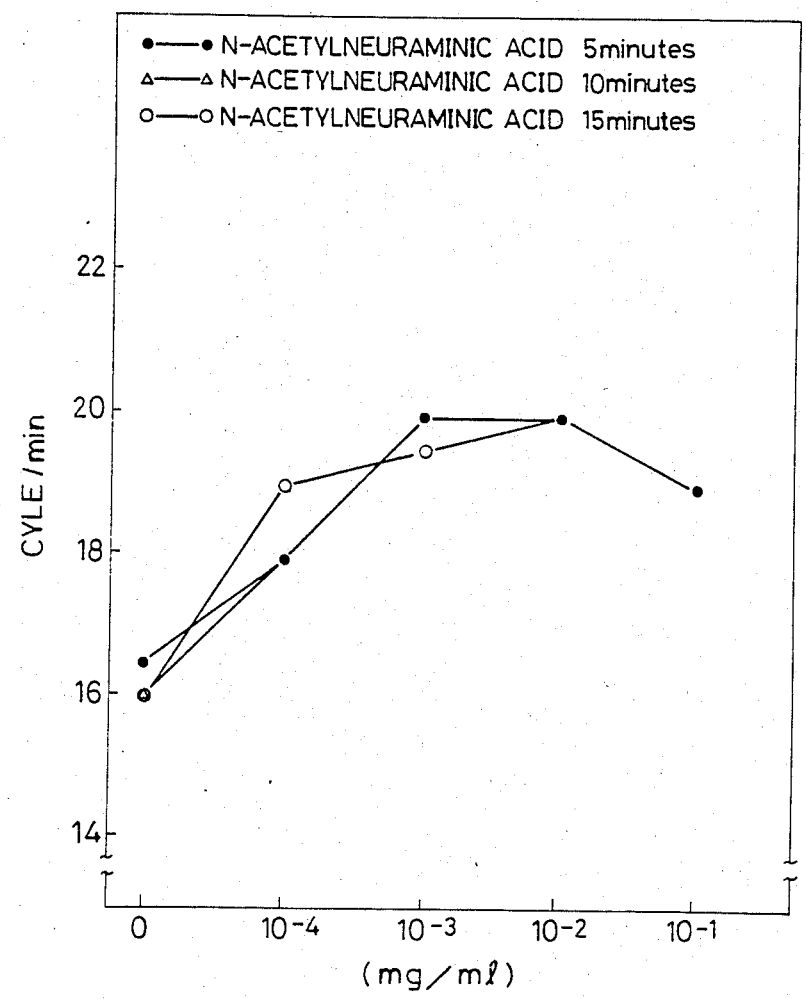
Figure 3:
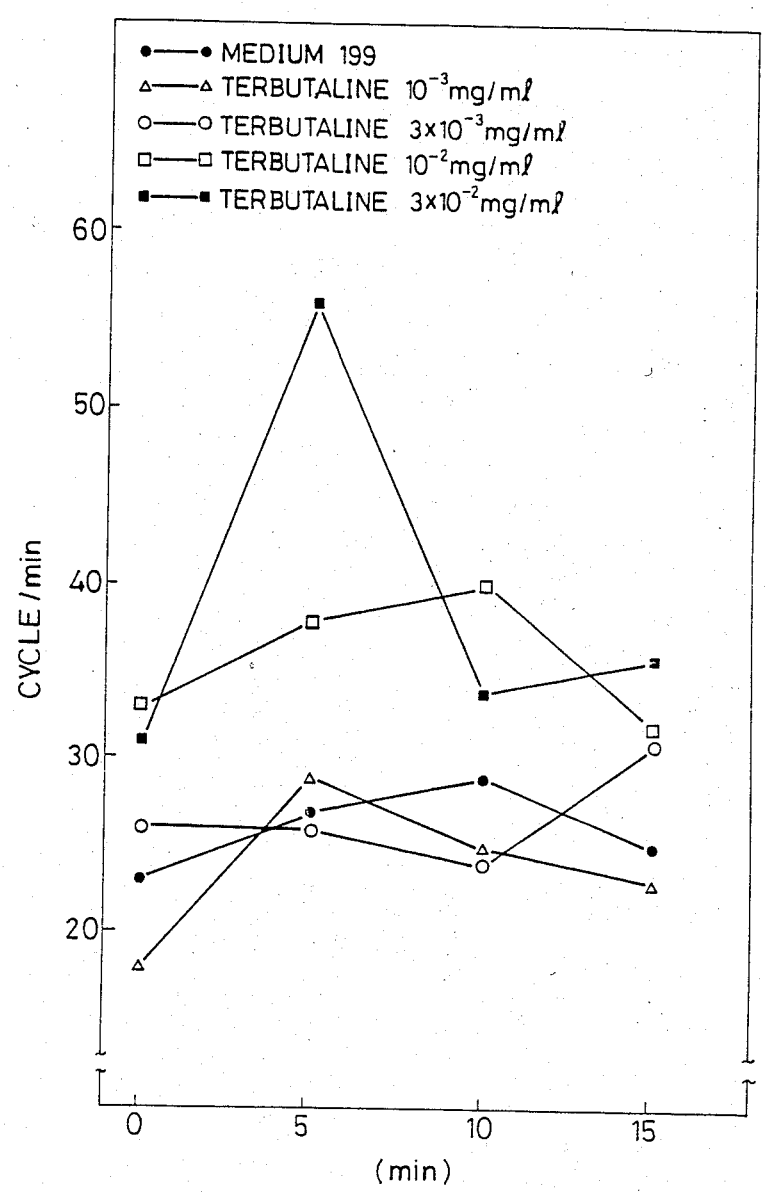
FIGS. 3 and 4 are illustrations of effect of terbutaline and acetylcholine on the rotation of ciliated cells.
Figure 4:
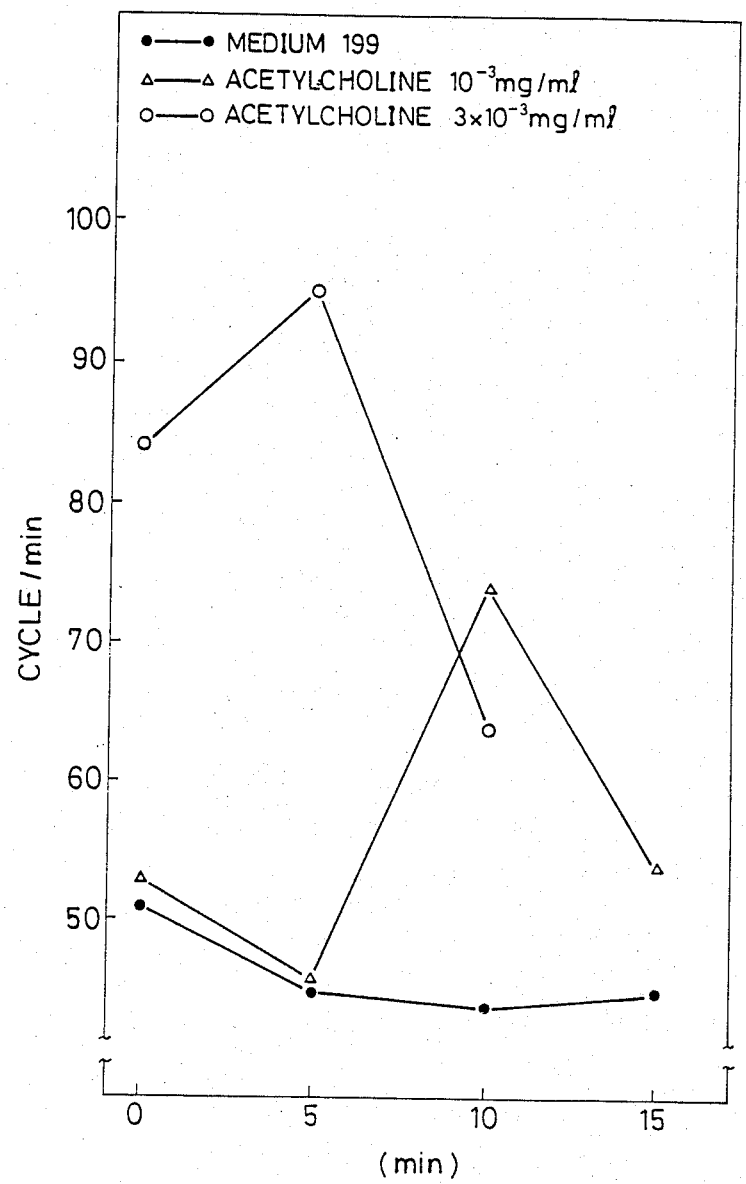

With application of N-acetylneuraminic acid ($10^{-4}$ to $10^{-1}$ mg/ml), the rotary motion of the cilium cells is gradually accelerated starting immediately after the application. 5 minutes, 10 minutes and 15 minutes after the application, plateaus were observed at application rates of $10^{-3}$ to $10^{-2}$ mg/ml. In these plateaus, the speed in revolutions per minute was about 25% higher than that in the Medium 199, as will be seen from FIGS. 1 and 2. It was confirmed also that the rotary motion of the cilium cells is increased by application of $10^{-3}$ to $3 \times 10^{-2}$ mg/ml of terbutaline (5-[2-[(1.1-dimetylethyl)amino]-1-hydoxyethyl]-1,3-benzenediole), in a certain dependency to the dose. The effect was particularly remarkable 5 minutes after the application, as can be seen from FIG. 3.

It was confirmed also that the speed of rotary motion of the cilium cells is increased by the addition of $10^{-3}$ mg/ml and $3 \times 10^{-3}$ mg/ml of acetylcholine. Speed peaks of the rotary motion were observed about 10 minutes and 5 minutes after the application when the amounts of addition were respectively, $10^{-3}$ mg/ml and $3 \times 10^{-3}$ mg/ml. In both cases, the rotary motion stopped 13 minutes after the application.

(Judgement)

It was confirmed that terbutalin and acetylcholine, which are known as being effective in promoting ciliary beat, promote also the rotary motion of the cilium cells. N-acetylneuraminic acid was confirmed as also being effective in the promotion of the rotary motion of ciliated cells. It is considered that the rotary motion of the ciliated cells is transmitted into ciliary beat, thereby facilitating the expectoration. This clearly shows that N-acetylneuraminic acid will be effective as an expectorant.

EXAMPLE 5

Effect of N-acetylneuraminic Acid on Sputum (Object)

Mucociliary transport rate (hereinunder referred to as MTR), i.e. the rate of transport of sputum by cilia, was measured using frog palatine mucosa. At the same time, physicochemical properties of the sputum before and after application of N-acetylneuraminic acid were compared.

(Method)

The sputum used as the specimens was collected from 12 samples of patients suffering from chronic obstructive lung disease. N-acetylneuraminic acid was added to the specimen sputum in the ratios of 5 mg/ml sputum and 1 mg/ml sputum, and the specimen was left for 1 hour at 4° C. before measurement. Sputum which has not been treated by N-acetylneuraminic acid was used as a comparison example. A palatine mucosa obtained from a decapitated frog head was kept at constant temperature and humidity until the mucus liquid of the frog itself depleted. The specimen sputum was placed on the dried palatine mucosa, and the speed of movement of the sputum was observed through a noumenal microscope, thus measuring the MTR. The pH value of the sputum was measured by means of an electronic model HM-SAp pH meter, while the spinnability was measured by a device developed by Nagaoka and Yamanaka (disclosed in Transactions of 2nd Symposium of Cough and sputum, published July 20, 1979). The yield value was measured by Dulfano's double-tube method which is shown in the American Review of Respiratory Diseases, Vol. 104, p88, 1971.

(Result)

As shown in Table 4, five out of six samples treated with 1 mg/ml of N-acetylneuraminic acid showed a reduction in pH value (pH 7.31 0.40), while the remaining one sample showed a slight increase in pH value. Increase in the yield value was observed in three samples, while three samples showed a reduction. The yield value was unchanged in the remaining one sample. As to the spinnability, five samples showed a reduction, while one sample showed a slight increase. The samples which showed reduction in the spinnability exhibited a tendency to increased MTR.

TABLE 4
Effect of N—acetylneuraminic Acid or Sputum

| No. | Treatment | Appearance | Amount ml | pH | Yield value mmH$_2$O | Spinnability mm | MTR mm/min |
|---|---|---|---|---|---|---|---|
| 1 | B* | M | 2 | 7.72 | 3.7 | 55 | 19 |
|   | A** |   |   | 7.35 | 11.5 | 19 | 38 |
| 2 | B | M | 2 | 7.52 | 0.1 | 10 | 8 |
|   | A |   |   | 7.62 | 0.1 | 3 | 19 |
| 3 | B | P | 2 | 7.98 | 2.7 | 5 | 20 |
|   | A |   |   | 7.20 | 0.7 | 2 | 27 |
| 4 | B | M | 2 | 6.98 | 1.9 | 22 | 25 |
|   | A |   |   | 6.84 | 3.2 | 12 | 29 |
| 5 | B | M | 2 | 7.24 | 2.2 | 18 | 18 |
|   | A |   |   | 6.94 | 3.1 | 16 | 30 |
| 6 | B | M | 2 | 8.16 | 14.3 | 22 | 15 |
|   | A |   |   | 7.88 | 7.5 | 26 | 18 |

B*: Before treatment by N—acetylneuraminic acid (2 mg)
A**: After treatment by N—acetylneuraminic acid (2 mg)
P: Pus sputum
M: Viscous sputum

EXAMPLE 6

Acute Toxicity Test of N-acetylneuraminic Acid

A test was conducted to examine the acute toxicity of N-acetylneuraminic acid, using mice and rats, by means of intravenous injection, subcutaneous injection, per os inhalation.
(1) Test Animals
ICR mice: 6 weeks old
SD rats: 6 weeks old (7 weeks old in case of inhalation)
(2) Application Density
13 to 15% (W/V) dissolved in distilled water
(3) Number of Test Animals per Level
10
(4) Observation Period
14 days (5) Method of Calculation fo LD$_{50}$
By Litchfield-Wilcoxon method. The result of the test is shown in Table 5 below.

TABLE 5

| | LD$_{50}$ (mg/kg) | | | |
| | mice | | rats | |
| Route | M | F | M | F |
|---|---|---|---|---|
| intravenous | 1700 (1441–2008) | 2500 (2137–2925) | 1870 (1748–2001) | 1880 (1741–2030) |
| subcutaneous | >5000 | >5000 | >5000 | >5000 |
| per-os | >5000 | >5000 | >5000 | >5000 |
| inhalation | — | — | >4.33 g/m$^3$ | >4.33 g/m$^3$ |

Inhalation was conducted by 1-hr exposure to mist.
Values in parentheses show 95% reliability level.

EXAMPLE 7

Synthesis of Sodium Salt of N-Acetylneuraminic acid

A small amount of activated carbon was added to an aqueous solution of N-acetylneuraminic acid and, under a flow of nitrogen gas, 1N sodium hydroxide was added to obtain a pH value of pH 7.3 to 7.8. The reacted solution was filtered using a filter of 0.2 μm and the filtrate was freeze-dried, forming a colorless powder of sodium salt of N-acetylneuraminic acid.

1R 3400 cm$^-$, 2937 cm$^-$, 1660 to 1620 cm$^{-1}$, 1560 cm$^{-1}$, decomposition point: about 140°–185° C., (decomposition with foaming) $^1$H-400 MHz (D$_2$O); 1,807 (dd, H3ax); 2,205 (dd, H3eq); 4,022 (m, H4); 3,901 (t, H5); 3,973 (d, H6); 3,501 (d, H7); 3,747 (m, H8); 3,598 (dd, H9'); 3,831 (dd, H9); 2,041 (s, Ac-5).

EXAMPLE 8

Effect of Sodium Salt of N-Acetylneuraminic Acid on Ciliary Movement of Palatine Mucosa of Frog Using the sodium salt of N-acetylneuraminic acid obtained in Example 7, a test was conducted to confirm the above-mentioned effect in accordance with the same testing method as that of Example 1. The result of this test is shown in Table 6.

From Table 6, it will be seen that the sodium salt of N-acetylneuraminic acid caused acceleration of the MTR of the frog palatine mucosa in a certain dependency on the dose. The result was subtantially equivalent to that of the acetylcholine (comparison agent) at a concentration of 10$^{-4}$ mg/ml. This suggests that the sodium salt of N-acetylneuraminic acid produces an effect similar to that produced by the above-described N-acetylneuraminic acid and its calcium salt.

TABLE 6

Effect of Sodium Salt of N—Acetylneuraminic Acid on Mucociliary Transport
Acceleration: mean value ± standard deviation (%*)

| agent | amount of addition (mg/ml) | N | time after applied (min) 5 | 10 | 15 |
|---|---|---|---|---|---|
| control | — | 8 | −1.6 ± 6.3 | −11.9 ± 10.8 | −7.4 ± 9.8 |
| sodium salt of N—acetyl- neuraminic acid | $10^{-4}$ | 8 | 2.6 ± 22.2 | 8.5 ± 21.9 | 7.1 ± 27.2 |
| | $10^{-3}$ | | 16.2 ± 19.5 | 18.9 ± 22.1 | 17.7 ± 34.0 |
| | $10^{-2}$ | | 20.8 ± 25.5 | 18.0 ± 29.7 | 5.7 ± 24.9 |
| | $10^{-1}$ | | 10.7 ± 19.2 | 8.5 ± 23.4 | 7.4 ± 24.7 |
| acetylcholine | $10^{-4}$ | 8 | 3.0 ± 7.6 | 3.8 ± 15.5 | −5.5 ± 10.0 |
| | $10^{-3}$ | | 12.3 ± 8.5 | 19.9 ± 16.8 | 13.9 ± 20.5 |
| | $10^{-2}$ | | 17.5 ± 14.3 | 18.8 ± 21.1 | 24.9 ± 25.6 |
| | $10^{-1}$ | | 22.8 ± 26.1 | 31.0 ± 24.9 | 30.5 ± 19.5 |

Acceleration (%) = $\left(1 - \frac{\text{Transport Rate in Drug}}{\text{Transport Rate in Control}} - 1\right) \times 100$ Over 20.0% is judged as significant.

EXAMPLE 9

Effect of Sodium Salt of N-Acetylneuraminic Acid on Rotary Motion of Ciliated Cell A test was conducted to examine the above-mentioned effect by using sodium salt of N-Acetylneuraminic Acid, in accordance with the same testing method as that of Example 2. The result of this test is shown in Table 7 which shows the following facts.

A significant number of rotations was observed upon application of $10^{-3}$ mg/ml of sodium salt of N-acetylneuraminic acid.

Terbutaline showed a general tendency of increase of the rotation at concentration of $10^{-4}$ to $10^{-}$ mg/ml.

Acetylcholine showed an increase in the rotation in a certan dependency on the dose, at the concentration of between $10^{-3}$ and $10^{-2}$ mg/ml.

From these facts, it is understood that the sodium salt of N-acetylneuraminic acid can be used as an expectorant as an expectorant as effectively as N-acetylneuraminic acid and its calcium salt.

EXAMPLE 10

Effect of Sodium Salt of N-Acetylneuraminic Acid on Sputum

Effect of sodium salt of N-acetylneuraminic acid on sputum was examined in accordance with the testing method explained in connection with Example 5. The result of this test is shown in Table 8.

From FIG. 8, it will be seen that the samples treated by sodium salt of N-acetylneuraminic (1 mg/ml sputum) showed a significant increase in pH value and MTR. Although the spinnability was generally increased, a reduction was observed with regard to the yield value.

From these facts, it is understood that the sodium salt of N-acetylneuraminic acid can be used effectively as an expectorant which increases the viscosity of low viscosity sputum such as purulent sputum which is difficult to expectorate to a high level suitable for transport by cilia, thereby facilitating the expectoration.

TABLE 8

Rheological properties before and after Sodium Salt of N—Acetylneuraminic Acid Treatment of purulent sputum from patients with diffuse panbronchiolitis

| | Treatment | Number of specimens | Mean ± S.D. |
|---|---|---|---|
| MTR (mm/min.) | before | 15 | 9 ± 5 |
| | after | 15 | 12 ± 5$^a$ |

TABLE 7

Effect of Sodium Salt of N—acetylneuraminic Acid on Rotating Ciliated Explant
Acceleration: mean value ± standard deviation (%*)

| Drug | Dose (mg/ml) | N | time after perfusion (min) 5 | 10 | 15 |
|---|---|---|---|---|---|
| control | — | 8 | 1.0 ± 5.8 | −0.9 ± 6.8 | −1.9 ± 6.8 |
| terbutaline | $10^{-4}$ | 3 | −5.2 ± 12.2 | 1.6 ± 4.6 | 6.7 ± 3.0 |
| | $10^{-3}$ | | 51.2 ± 36.0 | 37.2 ± 35.5 | 42.1 ± 32.8 |
| | $1-^{-2}$ | | 18.6 ± 0.3 | 24.8 ± 3.5 | 2.7 ± 7.4 |
| acetylcholine | $10^{-4}$ | 2 | −1.7 + 13.4 | 0.8 + 12.8 | 14.6 + 6.8 |
| | $10^{-3}$ | | 27.8 ± 12.2 | 10.6 ± 15.0 | 20.8 ± 26.4 |
| | $10^{-2}$ | | 58.1 ± 38.1 | 52.0 ± 32.6 | 44.5 ± 22.0 |
| sodium salt of N—acetyl- neuraminic acid | $10^{-4}$ | 7 | −3.4 ± 9.7 | 0.6 ± 10.6 | −5.0 ± 8.2 |
| | $10^{-3}$ | | 11.6 ± 29.8 | 20.7 ± 27.5 | 16.2 ± 32.3 |
| | $10^{-2}$ | | 1.5 ± 11.6 | 2.1 ± 18.2 | 3.7 ± 29.3 |
| | $10^{-1}$ | | 0.0 ± 5.8 | 4.7 ± 6.6 | 15.4 ± 9.3 |

*Acceleration (A %) = $\left(1 - \frac{\text{Cycle in Drug}}{\text{Cycle in Control}} - 1\right) \times 100$ A > 20.0 is significant.

TABLE 8-continued

| Rheological properties before and after Sodium Salt of N—Acetylneuraminic Acid Treatment of purulent sputum from patients with diffuse panbronchiolitis | | | |
|---|---|---|---|
| | Treatment | Number of specimens | Mean ± S.D. |
| pH | before | 15 | 7.48 ± 0.41 |
| | after | 15 | 7.91 ± 0.43[b] |
| Yield value, mm$H_2O$ | before | 15 | 0.8 ± 1.5 |
| | after | 15 | 0.3 ± 0.6 |
| Spinnability, mm | before | 15 | 13 ± 14 |
| | after | 15 | 21 ± 28 |

[a]P < 0.01
[b]P < 0.001

EXAMPLE 11

Acute Toxicity Test of Sodium Salt of N-Acetylneuraminic Acid

A test was conducted to examine the acute toxicity of sodium salt of N-acetylneuraminic acid, using mice, rats, and guinea pig by means of per as, subcutaneous injection, intravenous injection, intraperitoneal injection, and inhalation.

(1) Test Animals

ICR mice: 6 weeks old

SD rats: 6 weeks old

Hartley guinea pig: 6 weeks old (2) Application Density

20% (W/V) dissolved in distilled water (3) Number of Test Animals per Level

10

(4) Observation Period 14 days (5) Method of Calculation of $LD_{50}$

By Probit Method. The result of the test is shown in Table 9 below.

TABLE 9

Acute Toxicity Test of Sodium Salt of N—Acetylneuraminic Acid

| | $LD_{50}$ (mg/kg) Way of dosage | | | | |
|---|---|---|---|---|---|
| Species | per os | subcutaneous injection | intraperitoneal injection | intravenous injection | inhalation |
| mouse | >5,000 | >5,000 | >5,000 | 6,286 (5,679-7,084) | — |
| | >5,000 | >5,000 | >5,000 | 7,951 (7,214-9,073) | — |
| rat | >5,000 | >5,000 | >5,000 | 2,966 (2,638-3,342) | >4,000 mg/m$^3$ |
| | >5,000 | >5,000 | >5,000 | >5,000 | >4,000 mg/m$^3$ |
| guinea pig | — | — | — | 2,856 (2,355-4,087) | — |

TABLE 9-continued

Inhalation was conducted by 1-hr exposure to mist.
Values in parentheses show 95% reliability limit.

What is claimed is:

1. An expectorant, comprising an effective amount of the compound of the formula I

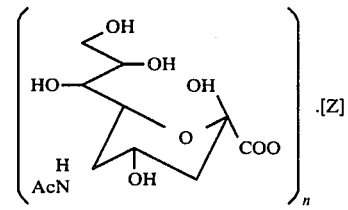

wherein, n=1 or 2, and on condition of n=1, Z represents hydrogen, lithium, potassium, sodium, ammonium, organic ammonium or organic amine, whereas on condition of n=2, Z represents calcium, barium or magnesium, together with a pharmaceutically acceptable carrier in a powdered form suitable for aerosol application.

2. An expectorant, comprising an effective amount of the compound of formula I of claim 1 and a pharmaceutically acceptable carrier, said expectorant being encapsulated.

3. The expectorant of claim 1, wherein said pharmaceutically acceptable carrier is lactose.

4. A method of promoting expectoration, comprising administering to a human being by inhalation, an effective amount of the compound of formula I, 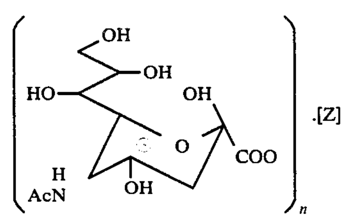 wherein n=1 or 2, and on condition of n=1, Z represents hydrogen, lithium, potassium, sodium, ammonium, organic ammonium or organic amine, whereas on condition of n=2, Z represents calcium, barium or magnesium.

5. The method of claim 4, wherein said administration is achieved by use of a liquid or powdered aerosol.

6. The method of claim 4, wherein said compound of formula I is combined with a pharmaceutically acceptable carrier.

7. The method of claim 6, wherein said carrier comprises lactose.

8. The method of claim 4, wherein said administration is in doses of 0.5-5 mg.

* * * * *